United States Patent [19]

Hauri

[11] Patent Number: 4,820,284

[45] Date of Patent: Apr. 11, 1989

[54] SUCTION DEVICE FOR THE DRAINAGE OF WOUNDS AND USE OF THE DEVICE

[75] Inventor: Hermann Hauri, Oensingen, Switzerland

[73] Assignee: Genossenschaft VEBO Solothurnische Eingliederungsstätte für Behinderte, Oensingen, Switzerland

[21] Appl. No.: 41,297

[22] Filed: Apr. 22, 1987

[30] Foreign Application Priority Data

Apr. 24, 1986 [CH] Switzerland .......................... 1684/86

[51] Int. Cl.[4] .............................................. A61M 1/00
[52] U.S. Cl. ................................................ 604/318
[58] Field of Search .......................... 604/317–319; 116/266, 268, 269, 270; 215/365, 270, 271

[56] References Cited

U.S. PATENT DOCUMENTS

| 3,334,628 | 8/1967 | Saemann et al. | 604/318 |
| 4,063,556 | 12/1977 | Thomas et al. | 604/318 |
| 4,675,010 | 6/1987 | Siposs et al. | 604/319 |

FOREIGN PATENT DOCUMENTS

| 0066699 | 12/1982 | European Pat. Off. . |
| 0175830 | 4/1986 | European Pat. Off. . |
| 584037 | 1/1977 | Switzerland . |
| 605313 | 12/1977 | Switzerland . |

Primary Examiner—C. Fred Rosenbaum
Assistant Examiner—J. L. Kruter
Attorney, Agent, or Firm—Spencer & Frank

[57] ABSTRACT

The suction device comprises a suction vessel with a cover, the latter being provided with a projecting member. A rubber-like elastic membrane is fixedly mounted onto the top part of the projecting member. The cover comprises a first connector having its passage connected with the inner space of the suction vessel, and a second connector having its passage connected with a chamber bounded by said projecting member and the membrane. The two connectors are connected with each other by means of a connecting hose, shortly before evacuating the inner space of the suction device, at the latest, with the result that the same negative pressure will prevail in the chamber as in the inner space of the suction device. For carrying out the wound drainage the connecting hose is detached from the connector pertaining to the chamber and is connected with a suction conduit leading to the wound. It is thus possible to avoid—during the time of storage elapsed between putting the evacuated suction device in a state of readiness and using it for wound drainage—any effects of fatigue in the membrane as well as any passage of gas through the membrane into the inner space of the suction vessel, by diffusion, even if the membrane is designed thin.

12 Claims, 2 Drawing Sheets

SUCTION DEVICE FOR THE DRAINAGE OF WOUNDS AND USE OF THE DEVICE

BACKGROUND OF THE INVENTION

1. Field of the Invention

The invention refers to a suction device for the drainage of wounds. A device of this kind comprises a suction vessel, a connection hose fastened to said suction vessel and adapted to connect the inner space of said suction vessel with a suction conduit. Furthermore, there is provided a clamp for compressing the connection hose, and an indicating device for indicating the pressure difference between the surrounding atmosphere and said inner space. The indicating device comprises an elastically deformable membrane mounted on said suction vessel and provided with a first surface bounding said inner space and a second surface facing away from said inner space. The invention equally refers to the use of the device for the drainage of wounds.

2. Description of the Prior Art

A suction device known from Swiss Pat. No. 605 313 comprises a suction vessel provided on top with an opening adapted to be closed by means of a plug. The plug made of a rubber-like material comprises a connection hose continuous therewith and adapted to be blocked by means of a clamp, the connection hose serving the purpose of connecting a suction conduit to the device, and being arranged to comprise a section thinned out to form a membrane comprising two horns protruding toward the outside. The membrane constitutes—together with the horns—an indicating device adapted to indicate the difference in presence existing between the surrounding atmosphere and the inner space of the suction vessel. As a matter of fact, if a negative or suction pressure exists in the inner space of the suction vessel relative to the surrouding atmosphere, then the membrane, which in relaxed state shows a plane configuration, will curve inwardly, so that the position of the horns connected with the membrane will represent a measure for the value of the suction pressure. The membrane undergoes continuous deformation while it is being stored, from the time of evacuation of the suction vessel to the time the latter is used for wound drainage, with the result, that the membrane will show effects of fatigue and may even undergo plastic deformation. This time duration will frequently amount to several weeks or months. If the suction vessel then is used for wound drainage, then the membrane will fail to return exactly to its original relaxed state. This causes a negative pressure to be indicated and this reading is incorrect because there is no longer any substantial pressure difference. The error in indication of the negative pressure will be larger, the longer the time elapsed between the evacuation of the suction vessel and its use for wound drainage. Indicating devices which are built according to or similar with that of Swiss Pat. No. 605 313 are unsuitable as suction vessels with long time durations between evacuation and use, even if the suction vessel is meant to be used only once. In addition, the accuracy in determining the value of the negative pressure using the suction device of Swiss Pat. No. 605 313 becomes further reduced by virtue of the fact, that the deformation of the membrane caused by the negative pressure is relatively small. This reduced accuracy is because of the comparatively large ratio between the thickness and the surface area of the membrane. A smaller ratio between the thickness and the area of the membrane would have the result, that during the storage time of the evacuated suction vessel the incurring fatigue and plastic deformation of the membrane would be greater. Also, a reduction in the thickness of the membrane would result in increased danger, that gas will pass through the membrane into the inner space of the suction vessel by diffusion. Furthermore, the indicating device of the known suction device possesses no scale of any kind, so that the determination of the pressure with any degree of accuracy is difficult.

SUMMARY OF THE INVENTION

Hence from what has been explained heretofore it should be apparent that the art is still in need of a suction device for the drainage of wounds which is not associated with the aforementioned drawbacks and limitations of the state-of-the-art proposals.

It is therefore a primary object of the present invention to provide a novel suction device for the drainage of wounds which is not associated with the drawbacks and limitations of the prior art as heretofore discussed and which effectively and reliably fulfills an existing need in the art.

Another and more specific object of the invention relates to a new and improved suction device for the drainage of wounds, which specifically provides for the possibility of more accurately determining the pressure difference between the surroundings and said inner space of said suction device. Another object of the invention is to allow the manufacturing of the indicating device as well as the entire suction device at low cost, thereby making it economically feasible to provide a suction device for a single use.

The foregoing and other objects are attained in accordance with one aspect of the invention by providing a chamber bounded by the second surface of the membrane and a portion of a projecting member of the suction vessel. The projecting member of the suction vessel is provided with a connector adapted to be detachably connected with one end of a connection hose. The other end of the connection hose is in turn connected to a suction conduit.

The invention also concerns a use of the suction device in the course of which the inner space of the suction vessel is at least partially evacuated prior to using the device for wound drainage.

The invention possesses a series of advantages. The suction device according to the invention may be stored between the time the inner space of its suction vessel is at least partially evacuated and the time it is used for sucking off wound secretions. In the stored state, no pressure difference exists above the membrane, i.e. between the chamber and the inner space of the suction vessel. This guarantees, that even with a small thickness of the membrane, the latter will maintain its elasticity during the storage of its evacuated suction vessel and will not show effects of fatigue. It further guarantees that during storage neither air nor any component thereof will pass through the membrane into the inner space of the suction vessel by diffusion. The suction device with evacuated suction vessel may therefore be stored several weeks or months, or even as long as a year, without the aforementioned disadvantages. The possibility of designing the membrane comparatively thin in relation to the surface area of its free section disposed between the chamber and the inner space of the suction vessel provides the decided advantage, that the membrane will be deformed to a relatively large degree by the pressure difference. This allows the magnitudes or values of the pressure difference to be read off with ease and accuracy.

BRIEF DESCRIPTION OF THE DRAWINGS

The invention will be better understood and objects other than those set forth above will become apparent when consideration is given to the following detailed description thereof. Such description makes reference to the annexed drawings wherein.

DETAILED DESCRIPTION OF THE PREFERRED EMBODIMENTS

Figure 1:
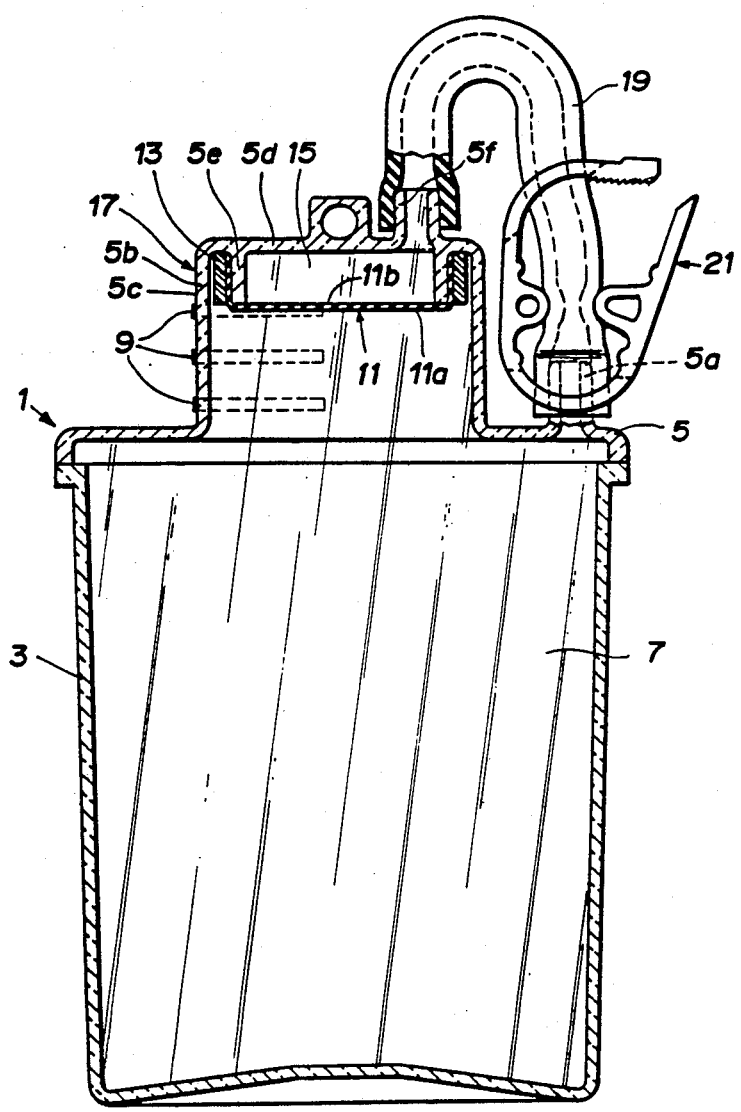
FIG. 1 shows a vertical section through the suction vessel of a suction device in a state in which the same pressure prevails on both sides of the membrane.
Figure 2:
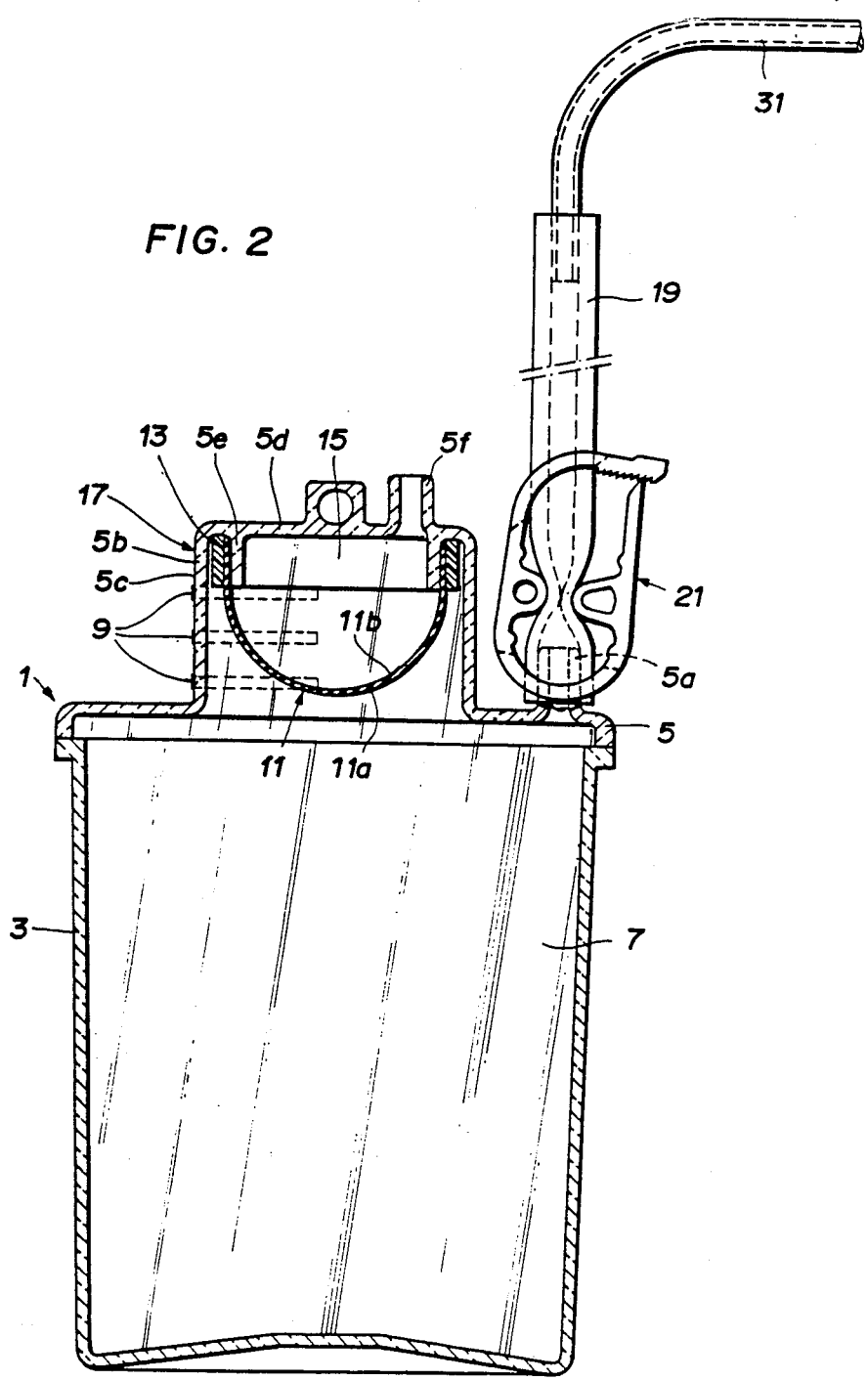
FIG. 2 shows a vertical section through the suction vessel of the suction device shown in FIG. 1, the membrane being deformed by virtue of a difference in pressure.

The suction device shown in FIGS. 1 and 2 is provided for wound drainage and comprises a suction vessel 1 intended to be used only once. The suction vessel 1 or more accurately its wall, is made of two parts, a container 3 and a cover 5 rigidly and non-separably connected by welding to the container 3. The container 3 and the cover 5 define an inner space 7. The cover 5 comprises near its outer edge a connector 5a shaped as a stud, and in its central part a projecting member 5b arranged to protrude out of the adjoining part of the cover 5 away from the suction vessel, i.e. in an upward direction. The projecting member 5b comprises a cylindrical jacket part 5c and a planar top part 5d. The top part 5d comprises a ring-shaped part 5e protruding into the inner space 7, and a stud-like connector 5f arranged to protrude upwardly and away from the inner space 7. Both the container 3 and the cover 5 consist of a colorless, transparent, clear plastic material of stable shape such as a copolyester commercially available under the name ARNITE. The material selected should remain transparent and clear even when sterilized with gamma rays. The projecting member 5b, or more accurately its jacket part 5c, is equipped with a scale 9, arranged to comprise for example three colored markings disposed at distances from each other in the longitudinal direction of the central axis of the jacket part 5c. The markings are arranged to at least partially surround said central axis in a curved or ring-like manner.

An elastic membrane 11 is rotationally symmetrical with respect to the central axis of the projecting member 5b. The elastic membrane 11 is made of a colored—for example orange—rubber-like elastic material such as nitrile rubber. The membrane 11 is arranged to enclose the outer cylindrical surface of the ring-shaped part 5e and to be held fast thereon by means of a cylindrical ring 13 pressed onto it. The edge of the sleeve ring 13 facing away from the top part 5d is at least approximately flush with the free end of the ring-shaped part 5e. The ring 13 is made of a plastic material of essentially stable shape, for example of the same copolyester mentioned in conjunction with the suction vessel 1. However, it is made opaque, at least to a certain extent, and arranged to have for example a whitish color, to make it cover the fixedly held peripheral section of the membrane 11. A first surface 11a of the central, free section of the membrane 11, i.e. of the section not held clamped between the ring-shaped part 5e and the ring 13, is arranged to bound the inner space 7 of the suction vessel 1. The second surface 11b of said central section of the membrane 11 that faces away from said inner space 7, together with the top part 5d of the projecting member 5b and the ring-shaped part 5e define a chamber 15. Even though this chamber 15 is located inside the walls of the suction vessel, it occupies a considerably smaller volume than the suction vessel inner space 7 proper. The connector 5a, or, more accurately, its through bore is pneumatically connected with the inner space of the suction vessel, whereas the through bore of the connector 5f is pneumatically connected with the chamber 15. The two essentially cylindrical studs providing the connectors 5a and 5f are both arranged to have approximately equal outer diameters. As will be explained in further detail, the projecting member 5b of the suction vessel and the membrane 11 constitute an indicating device 17 adapted to indicate the pressure difference existing between the chamber 15 and the inner space 7, i.e. the negative or suction pressure within the inner space 7.

A connector hose 19 is tightly but detachably connected to the connector 5a. The connection hose 19 is made of soft polyvinyl-chloride or polyurethane. A clamp 21 made of an elastically deformable thermoplastic material comprises two holes permeated by the connection hose 19; further, a number of grooves are provided at one end of the clamp and a sharp edge is provided at its other end with the edge being adapted to be removably snapped into one of said grooves. If the two ends of the clamp 21 are disconnected from each other, as shown in FIG. 1, then the clamp 21 will allow the connection hose 19 to freely pass therethrough. If, on the other hand, the end of the clamp 21 provided with the sharp edge is snapped into one of the grooves provided in the other end section of the clamp 21, as shown in FIG. 2, then the clamp 21 will clamp and squeeze the connection hose 19 in a way to tightly block any passage therethough.

The end of the connection hose 19 that faces away from the connector 5a may be detachably connected to the connector 5f, as shown in FIG. 1, or to the suction conduit 31 shown in FIG. 2. The suction conduit 31 comprises at least one hose or, in general, two hoses connected with each other by means of a coupling member, the one hose section destined to be inserted into the body of a patient being provided with drainage holes.

Now the manufacture, preparation and operation of the suction device will be explained. Subsequent to making the various individual parts, the membrane 11 is mounted onto the cover 5 by means of the ring 13. Then the container 3 and the cover 5 are mutually connected by friction welding, the connection hose 19 is mounted on to the connector 5a, and the clamp 21 is applied to the connection hose 19. The end of the connection hose 19 that faces away from the connector 5a may now be connected with a pumping and evacuating device not shown in the drawing, whereupon the inner space 7 may be evacuated through the passage of the connecting hose 19. During the evacuation the clamp 21 is set to unblock the passage of the connection hose 19. After the evacuation, the clamp 21 is closed or locked, to make it block the passage of the connection hose 19. The end of the connection hose 19 that faces away from the connector 5a may now, separated from the evacuating device, be fitted onto the connector 5f, immediately or relatively soon, such as after a few hours or days. Then, the clamp 21 is brought into the position shown in FIG. 1, in which position it will unblock the passage of the connection hose 19. Air will now flow from the chamber 15 and the connection hose passage into the inner space 7 of the suction vessel, causing a pressure equalization to take place between the inner space 7 and the chamber 15. This means that the pressure in the inner space 7 of the suction vessel will slightly rise, but will still remain considerably lower than the air pressure prevailing in the surroundings of the suction vessel. Subsequent to said pressure equalization there will exist a predetermined nominal or initial pressure difference between the surroundings of the suction vessel 1 and its inner space. Since the pressure difference existing between the chamber 15 and the inner space 7 will completely disappear thereby dropping to zero in the course of said equalization, the membrane 11 will assume the shape shown in FIG. 1, whereby the central face section of the membrane lies in the plane defined by the free edge of the ring-shaped part 5e. This position allows the membrane 11 to relax in a flat circular shape. Thus the membrane 11 is subject at the most to a relatively low stress produced and limited by the fixedly mounted state of the peripheral section of the membrane. The suction device is then wrapped into a plastic jacket, and the latter welded tight. The suction device is then sterilized by irradiation with gamma rays.

The suction device may now be delivered for example to a hospital and kept there for a number of days, weeks or months, until it will get to be used for wound drainage, and in particular for draining a surgical wound in the course of a surgical operation. If a wound drainage of this kind is to be performed, then the aforementioned jacket is removed from the suction device, the passage of the connection hose is blocked by clamping the clamp 21 tight, and the end of the connection hose 19 fitted onto the connector 5f is removed from the latter. Having removed the connection hose 19 from the connector 5f, air will flow from the surroundings through the passage of the hose 19 into the chamber 15. This will make the pressure in the chamber 15 greater than the pressure in the inner space 7, so that the membrane 11 or more accurately, its central free section will be stretched, deformed, and curved toward the inner space of the suction vessel in the manner shown in FIG. 2. Furthermore, the suction conduit 31 may now be placed with its one end into the surgical wound and with its other end into the connection hose 19. Furthermore the suction vessel may be suspended on a hook or the like, by means of its eye-like projection provided in the center of its top part 5d.

If as a result of the negative pressure existing in the inner space 7 of the suction vessel liquid wound secretions and perhaps solid particles contained therein and/or air and/or another gas will now be sucked into the inner space 7 of the suction vessel, then the pressure existing in said inner space 7 will mount in relation to the surrounding air pressure. The stretching and deformation of the membrane 11 will thereby decrease, with the result that its shape will once again slowly approach the shape shown in FIG. 1. The membrane 11 of the indicating device 17 will now show via the scale 9, the pressure difference existing between the chamber 15 and the inner space 7 of the suction vessel. A person controlling the suction device will be able to see the membrane 11 through the jacket part 5c and read off the value of said pressure difference. If the pressure difference drops to zero or to another predetermined minimum value, for example the top scale marking of FIGS. 1 and 2 or their vicinity, then the person taking care of the patient may clamp the connection hose 19 by means of the clamp 21 and detach it from the suction conduit 31. If it is necessary this person may then connect a different evacuated suction vessel to the suction conduit 31.

The diameter of the outer surface of the ring-shaped cylindrical part 5e, and the diameter of the central section of the membrane 11 which is deformable by the pressure difference is at least 20 mm, and for example 25 to 35 mm. The membrane 11 may be made comparatively thin and arranged to have a maximum thickness of 2 mm and preferably a maximum thickness of less than 1 mm, for example 0.3 to 0.9 mm. The thickness of the membrane 11 will thus amount to a maximum of 10% and preferably a maximum of 5% of the diameter of the central deformable section of membrane 11. Since the last-mentioned diameter is relatively large compared to the thickness of the membrane, the membrane 11 will—in case the pressure difference to be determined possesses its nominal or initial value—become curved to a comparatively large degree, from the free edge of the ring-shaped part 5e toward the inner space 7. The displacement that the center of the membrane 11 carries out between the two extreme positions shown in the FIGS. 1 and 2 has a value of at least 7 mm, preferably 10 mm and for example approximately 15 mm. In addition the membrane is fully visible around the circumference of and through the jacket part 5c. The indicating device 17 thus enables a person to read off the value of the pressure difference existing between the chamber 15 and the inner space 7 with comparative accuracy and without any appreciable effort.

The markings provided at the two ends of the scale 9 may be identified for example as "MAX" and "MIN". Also, the aforementioned nominal or initial pressure difference between the surroundings and the inner space 7 of the suction vessel may be determined as required, depending on the sensitivity of the bodily region containing the wound to be treated. It would be possible, for instance, to provide two types of suction devices, the nominal or initial pressure difference being about 90 kPascal in the first type and about 30 kPascal in the second type. In such a case the scale 9 may be made to have different distances between markings for the two types, with the result, that upon prevalence of the nominal or initial pressure difference the center of the membrane will be—for both types—at the marking located the farthest from the top part 5d, in spite of the differences in membrane deformations. It would be possible, instead, to equip the two types with membranes having different thicknesses, so that upon prevalence of the nominal or initial pressure difference, the two types will become deflected to similar degrees.

The processes of making and evacuating the suction vessel could be modified in a sense to have the two connectors 5a and 5f pneumatically connected to the connection hose 19 previous to mutually welding the container 3 and the cover 5 together. In this case the two suction vessel components could be welded to each other inside the hollow space of a manufacturing device evacuated to the predetermined nominal or initial negative pressure. In this way, it is already in the manufacturing state of the evacuated suction vessel that the negative pressure within the chamber 15 will be equal to that prevailing in the inner space 7.

The suction devices themselves may also be modified in various respects. The membrane could be provided for example with at least one horn-like and/or rod-like and/or lug-shaped indicating element disposed centrally or non-centrally with respect to the membrane and made of one piece therewith or being connected with it in some other manner, said element to be adapted to be displaced upon deformation of the membrane and, in case of non-central arrangement, to be swivelled too. The indicating element may be disposed either on the side of the membrane facing the inner space of the suction vessel, or on its side facing the chamber. It may, furthermore, be located completely inside the suction vessel walls and be made visible through a transparent region of said walls. If the indicating element is located on the side of the membrane that bounds the chamber, it would be possible to position said indicating element, and the connector stud belonging to the chamber, coaxially with the central axis of the projecting member that carries the membrane and also passes through the center of the membrane. Also, the length dimension of the indicating element could be selected to have it permeate the chamber and the passage of the stud and to protrude from the latter outwardly, into the surroundings of the suction vessel. If the connecting hose is detached from the connector stud belonging to the chamber, then the part of the indicating element that protrudes from said stud would be directly visible, i.e. without having to look through the wall of the suction vessel. If an indicating element arrranged and built in the one or the other manner were provided, said element could serve to a certain extent as a pointer, whereby a corresponding scale could be provided.

The suction device may also be designed to have the suction vessel be used more than once. For this purpose, the suction vessel could be equipped with an opening adapted to be closed by means of a removable closing member, such as a plug or a cover. The indicating device may then be located directly on the wall of the suction vessel proper or on the closing member.

Obviously, numerous modifications and variations of the present invention are possible in the light of the above teachings. It is therefore to be understood, that within the scope of the appended claims the invention may be practiced otherwise than is specifically described herein. Accordingly,

What is claimed is:

1. Suction device for the drainage of wounds, the device comprising a suction vessel, a connection hose fastened to a first connector of said suction vessel and adapted to connect the inner space of said suction vessel with a suction conduit, a clamp for compressing the connection hose, and an indicating device adapted to indicate the pressure difference between the surroundings and said inner space and comprising an elastically deformable membrane mounted on said suction vessel and provided with a first surface bounding said inner space and a second surface facing away from said inner space, wherein said second surface of the membrane is arranged to bound, together with a member of said suction vessel, a chamber, and wherein said member of said suction vessel is provided with a second connector adapted to be detachably connected with one end of the connection hose when said inner space of the suction vessel is at least partially evacuated in turn to be connected to the suction conduit before performing a wound drainage, said member of said vessel comprises a ring-shaped part protruding towards said inner space and wherein the peripheral part of said membrane is fixedly mounted, by means of a ring, on a ring-shaped surface of said ring-shaped part, wherein said membrane including its peripheral, fastened part is arranged completely inside the vessel.

2. Suction device as claimed in claim 1, wherein the membrane and/or an element connected with said membrane is arranged to be visible from the outside through a transparent region of said suction vessel.

3. Suction device as claimed in claim 1, wherein each of said connectors of said member of said suction vessel is a stud, said connecting hose being adapted to be detachably connected to said stud.

4. Suction device as claimed in claim 1, wherein said vessel comprises a cover being provided with said first connector and wherein said member of said vessel is formed by a portion of said cover that protrudes out of the part of the cover comprising the first connector away from said suction vessel and comprises a cylindrical, transparent jacket part enclosing the membrane, and wherein the membrane are rotationally symmetrical in relation to the central axis of said jacket part.

5. Suction device as claimed in claim 4, wherein said jacket part of said suction vessel is adapted to serve as a carrier of a scale.

6. Suction device as claimed in claim 1, wherein said member of said suction vessel is non-detachably connected with the remaining wall of said suction vessel.

7. Suction device as claimed in claim 1, wherein said connection hose comprises a tube of polyvinyl-chloride.

8. Suction device as claimed in claim 1, wherein said connection hose comprises a tube of polyurethane.

9. Suction device as claimed in claim 1, wherein said inner space of said vessel is at least partially evacuated so that said device may perform a wound drainage and said connection hose is connected to said first connector and said second connector before the use of said suction device for the wound drainage.

10. Suction device as claimed in claim 1, wherein said vessel, said connection hose and said membrane are sterilized by irradiation.

11. A suctioning method using a suctioning device comprising a suction vessel, a connection hose fastened to a first connector of said suction vessel and adapted to connect the inner space of said suction vessel with a suction conduit, a clamp for compressing the connection hose, and an indicating device adapted to indicate the pressure difference between the surroundings and said inner space and comprising an elastically deformable membrane mounted on said suction vessel and provided with a first surface bounding said inner space and a second surface facing away from said inner space, wherein said second surface of the membrane is arranged to bound, together with a member of said suction vessel, a chamber, and wherein said member of said suction vessel is provided with a second connector adapted to be detachably connected with one end of said connection hose when said inner space of the suction vessel is at least partially evacuated in turn to be connected to the suction conduit before performing a wound drainage, said method comprising the steps of:
    partially evacuating the inner space of said suction vessel prior to its use for wound drainage;
    connecting the inner space of said suction vessel with said chamber at the latest after the evacuation through the connection hose;

compressing and closing off the connection hose by means of said clamp before the use of the suction vessel for wound drainage; and removing the end of the connection hose from said second connector.

12. A suction device connectable to a suction conduit for the drainage of wounds, comprising:

a suction vessel having first and second connectors;

a connection hose fastened to said first connector and adapted to connect the inner space of said suction vessel with the suction conduit;

means for indicating the pressure difference between the surroundings and the inner space, said indicating means comprising an elastic membrane having first and second surfaces, said membrane being mounted in said suction vessel so that said first surface of said membrane faces the inner space and said second surface of said membrane faces said second connector, whereby when said connection hose is connected to said first and second connectors, the pressures acting on said first and said second surfaces of said membrane are equalized and the inner space of said suction vessel is at least partially evacuated, in consequence of which said membrane is maintained in a relaxed state; and selectively operable clamping means for preventing the flow of fluid through said connection hose when the latter is not connected to said second connector or to said conduit.

* * * * *